(12) United States Patent
Tamori et al.

(10) Patent No.: US 9,128,083 B2
(45) Date of Patent: Sep. 8, 2015

(54) NONSPECIFIC ADSORPTION INHIBITOR OF SUBSTANCE RELATING TO LIVING BODY AND METHOD FOR COATING ARTICLE

(75) Inventors: Kouji Tamori, Chuo-ku (JP); Eiji Takamoto, Chuo-ku (JP); Toshihiro Ogawa, Chuo-ku (JP)

(73) Assignee: JSR CORPORATION, Tokyo (JP)

( * ) Notice: Subject to any disclaimer, the term of this patent is extended or adjusted under 35 U.S.C. 154(b) by 1249 days.

(21) Appl. No.: 12/267,001

(22) Filed: Nov. 7, 2008

(65) Prior Publication Data
US 2009/0124707 A1 May 14, 2009

(30) Foreign Application Priority Data

Nov. 9, 2007 (JP) ................. 2007-291793
Mar. 11, 2008 (JP) ................. 2008-061119

(51) Int. Cl.
| | |
|---|---|
| A61K 47/32 | (2006.01) |
| C08F 220/56 | (2006.01) |
| C08F 220/00 | (2006.01) |
| C08F 226/06 | (2006.01) |
| G01N 33/543 | (2006.01) |

(52) U.S. Cl.
CPC ........ *G01N 33/54393* (2013.01); *C08F 220/56* (2013.01)

(58) Field of Classification Search
CPC ..................... C08F 220/56; G01N 33/54393
See application file for complete search history.

(56) References Cited

U.S. PATENT DOCUMENTS

| | | | | |
|---|---|---|---|---|
| 3,845,066 A | * | 10/1974 | Vasta .................... | 524/247 |
| 6,730,740 B1 | * | 5/2004 | Mestach et al. ......... | 525/192 |
| 2006/0091015 A1 | | 5/2006 | Lau | |
| 2008/0160167 A1 | | 7/2008 | Tamori et al. | |

FOREIGN PATENT DOCUMENTS

| | | | |
|---|---|---|---|
| EP | 0 335 703 A2 | | 10/1989 |
| EP | 1790984 | * | 5/2007 |
| JP | 6-300761 | | 10/1994 |
| JP | 7-83923 | | 3/1995 |
| JP | 7-253430 | | 10/1995 |
| JP | 11-287802 | | 10/1999 |
| JP | 11-337552 | | 12/1999 |
| JP | 2002088311 | * | 3/2002 ........... C09D 201/00 |
| JP | 3443891 B2 | | 9/2003 |
| JP | 2005-513504 | | 5/2005 |
| JP | 2006-226982 | | 8/2006 |
| WO | WO 03/056338 A1 | | 7/2003 |
| WO | WO2006129670 | * | 12/2006 |

OTHER PUBLICATIONS

Holmlin et al., Zwitterionic SAMs that Resist Nonspecific Adsorption of Protein from Aqueous Buffer, Langmuir 2001, 17, 2841-2850.*
Ostuni et al., A Survey of Structure-Property Relationships of Surfaces that Resist the Adsorption of Proteins, Langmuir 2001, 17, 5605-5620.*
Ostuni et al., Self-Assembled Monolayers That Resist the Adsorption of Proteins and the Adhesion of Bacterial and Mammalian Cells, Langmuir 2001, 17, 6336-6343.*
JP 2002088311 Derwent abstract © 2012, p. 1-3, Derwent acount No. 2002-551481t.*
JP 2002088311 machine translation received from AIPN of the JPO on Mar. 6, 2012 p. 1-7.*
U.S. Appl. No. 12/602,138, filed Nov. 27, 2009, Tamori, et al.
M. Colonne, et al., "Binding of Streptavidin with Biotinylated Thermosensitive Nanospheres Based on Poly(N,N-diethylacrylamide-co-2-hydroxyethyl methacrylate)", Bioconjugate Chemistry, vol. 18, No. 3, XP002514293, May 2007, pp. 999-1003.
Marieta Nichifor', et al., "Copolymers of N-alkylacrylamides and styrene as new thermosensitive materials", Polymer, vol. 44, No. 10, XP004420100, May 1, 2003, pp. 3053-3060.
Kenji Kono, et al., "Coatings for easy removal of contaminates and production methods therefor", Database CA [Online] Chemical Abstracts Service, XP002514295, Mar. 27, 2002, 2 pages.
L. E. Coleman, et al., "Synthesis and Polymerization of N[2-Methyl-4-oxopentyl) ]-acrylamide-A New Reactive Vinyl Monomer", Journal of Polymer Science: Part A, vol. 3, XP002514294, 1965, 8 Pages.
U.S. Appl. No. 12/400,417, filed Mar. 9, 2009, Ogawa, et al.
U.S. Appl. No. 13/218,494, filed Aug. 26, 2011, Tamori, et al.
Office Action issued Jan. 24, 2012 in Japan Application No. 2008-061119 (With English Translation).
Combined Chinese Office Action and Search Report Issued Nov. 21, 2013, in Chinese Patent Application No. 200810176519.X with English translation.

* cited by examiner

*Primary Examiner* — Kortney L Klinkel
(74) *Attorney, Agent, or Firm* — Oblon, McClelland, Maier & Neustadt, L.L.P.

(57) ABSTRACT

A nonspecific adsorption inhibitor of a substance relating to a living body, which inhibits nonspecific adsorption of a substance relating to a living body such as various species of proteins which are used in clinical diagnostic agents, clinical diagnosis devices, biochips and the like, and a method for coating an article using said nonspecific adsorption inhibitor.

19 Claims, No Drawings

NONSPECIFIC ADSORPTION INHIBITOR OF SUBSTANCE RELATING TO LIVING BODY AND METHOD FOR COATING ARTICLE

BACKGROUND OF THE INVENTION

1. Field of the Invention

The present invention relates to a nonspecific adsorption inhibitor of a substance relating to a living body, which inhibits nonspecific adsorption of a substance relating to a living body such as various species of proteins which are used in clinical diagnostic agents, clinical diagnosis devices, biochips and the like, and to a method for coating an article using said nonspecific adsorption inhibitor.

2. Brief Description of the Background Art

In recent years, high sensitivity tests are required for the purpose of early stage detection of diseases and the like, and improvement of the sensitivity of diagnostic agents is a serious problem. Also in the case of a diagnostic agent which uses a solid phase such as a polystyrene plate and magnetic particle, for the purpose of improving sensitivity, the detection method is changing from the method which uses an enzymatic color development to a method which uses fluorescence or chemiluminescence from which more high sensitivity can be obtained. However, sufficient sensitivity has not been obtained actually. As a reason of this, in the case of a diagnosis in which a specific substance is detected in the coexistence of living body molecules such as serum, the coexisting living body molecules, secondary antibody, emission substrate and the like adhere nonspecifically to the solid phase, tools, container and the like. As a result, noises are increased to obstruct improvement of sensitivity. Accordingly, in the case of the diagnostic immunoassay, in order to reduce the lowering of sensitivity caused by the nonspecific adsorption of substances other than the specifically binding substance to the surface of the solid phase to be used in the immune reaction, as well as the tools and container, the noises are reduced generally by inhibiting the nonspecific adsorption through the use of a substance derived from organism such as albumin, casein and gelatin as a nonspecific adsorption inhibitor.

However, even when a nonspecific adsorption inhibitor by the conventional method is added, the nonspecific adsorption still remains. Furthermore, when a nonspecific adsorption inhibitor derived from a living body is used, there is a problem of organism pollution represented by BSE. Therefore, the development of a high performance nonspecific adsorption inhibitor by chemical synthesis is required.

As the nonspecific adsorption inhibitor by chemical synthesis, polymers having polyoxyethylene are proposed in JP-A-10-153599 and JP-A-11-352127, and a specific methacrylic copolymer in Japanese Patent No. 3443891. However, their nonspecific adsorption inhibitory effect was insufficient.

SUMMARY OF THE INVENTION

The present invention provides a nonspecific adsorption inhibitor of a substance relating to a living body, which can inhibit nonspecific adsorption of a substance relating to a living body such as protein to the solid phase surface and tools and container which are used in the diagnostic chemiluminescence immunoassay and the like, and a method for coating an article using said nonspecific adsorption inhibitor.

The nonspecific adsorption inhibitor for a substance relating to a living body according to an embodiment of the present invention comprises a copolymer comprising a repeating unit (A) represented by the following formula (1):

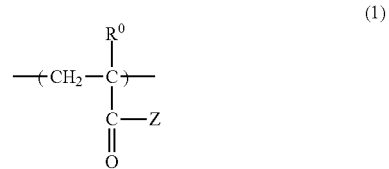

wherein $R^0$ represents a hydrogen atom or a methyl group and Z represents a group represented by the following formula (1a) or (1b):

wherein $R^1$ and $R^2$ independently represent a hydrogen atom, an alkyl group having from 1 to 8 carbon atoms or an alkyl group having from 1 to 8 carbon atoms which is substituted with at least one group selected from a hydroxyl group, a carboxyl group, an alkoxy group, an acyloxy group and an alkoxycarbonyl group;

wherein $R^3$ and $R^4$ independently represent single bond, methylene, methylene substituted with a hydroxyl group or a carboxyl group, an alkylene group having from 2 to 7 carbon atoms or an alkylene group having from 2 to 7 carbon atoms substituted with a hydroxyl group or a carboxyl group wherein total number of carbon atoms of $R^3$ and $R^4$ is from 4 to 10; wherein at least one of $R^3$ and $R^4$ may have an ether bond, and Y represents any one of a single bond, O and S and a repeating unit (B) represented by the following formula (2):

wherein $R^5$ represents a hydrogen atom or a methyl group and $R^6$ represents a phenyl group or a group represented by $-CO_2R^7$ wherein $R^7$ represents a substituted or unsubstituted alkyl group having from 1 to 12 carbon atoms, an alicyclic hydrocarbon or an aromatic hydrocarbon.

DETAILED DESCRIPTION OF THE INVENTION

With the aim of solving the problems described above, the inventors of the present invention have found that a copolymerized polymer of a specific composition has a high nonspecific adsorption inhibitory effect on a substance relating to a living body to accomplish the present invention.

According to the present invention, the substance relating to a living body means lipid, protein, saccharides or nucleic acids.

According to the above-mentioned formula (1) of the above-mentioned nonspecific adsorption inhibitor of a substance relating to a living body, $R^1$ may represent a hydrogen atom or a methyl group and $R^2$ may represent at least one species selected from a hydrogen atom, a methyl group and a hydroxyethyl group.

According to the above-mentioned nonspecific adsorption inhibitor of a substance relating to a living body, the aforementioned repeating unit (B) may be a structure derived from at least one monomer wherein its solubility in water is less than 20%.

According to the above-mentioned formula (2) of the above-mentioned nonspecific adsorption inhibitor of a substance relating to a living body, $R^5$ may represent a hydrogen atom or a methyl group, $R^6$ may represent $-CO_2R^7$ group and $R^7$ may represent at least one species selected from a methyl group, an ethyl group and a methoxyethyl group.

According to the above-mentioned nonspecific adsorption inhibitor of a substance relating to a living body, the aforementioned copolymer may further comprise a repeating unit (C) represented by the following formula (3):

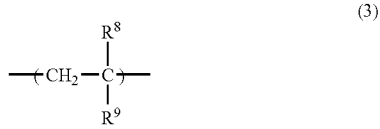

wherein $R^8$ represents a hydrogen atom or a methyl group and $R^9$ represents an organic group which comprises at least one aldo group or keto group.

According to the above-mentioned nonspecific adsorption inhibitor of a substance relating to a living body, it may further comprise a hydrazide compound (H) which comprises at least two hydrazino groups per one molecule.

The method for coating an article according to an embodiment of the present invention comprises a step of allowing an article to contact with a solution comprising the above-mentioned nonspecific adsorption inhibitor of a substance relating to a living body.

The following illustratively describes the nonspecific adsorption inhibitor of a substance relating to a living body according to an embodiment of the present invention and the method for coating an article using said nonspecific adsorption inhibitor.

1. Nonspecific Adsorption Inhibitor of a Substance Relating to a Living Body

1.1. Construction of the Nonspecific Adsorption Inhibitor of a Substance Relating to a Living Body 1. The nonspecific adsorption inhibitor of a substance relating to a living body concerned in this embodiment comprises a copolymer comprising a repeating unit (A) represented by the following formula (1):

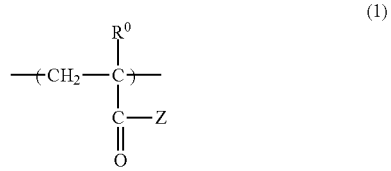

wherein $R^0$ represents a hydrogen atom or a methyl group and Z represents a group represented by the following formula (1a) or (1b):

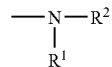

wherein $R^1$ and $R^2$ independently represent a hydrogen atom, an alkyl group having from 1 to 8 carbon atoms or an alkyl group having from 1 to 8 carbon atoms which is substituted with at least one group selected from a hydroxyl group, a carboxyl group, an alkoxy group, an acyloxy group and an alkoxycarbonyl group;

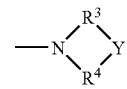

wherein $R^3$ and $R^4$ independently represent single bond, methylene, methylene substituted with a hydroxyl group or a carboxyl group, an alkylene group having from 2 to 7 carbon atoms or an alkylene group having from 2 to 7 carbon atoms substituted with a hydroxyl group or a carboxyl group wherein total number of carbon atoms of $R^3$ and $R^4$ is from 4 to 10, wherein at least one of $R^3$ and $R^4$ may have an ether bond, and Y represents any one of a single bond, O and S and a repeating unit (B) represented by the following formula (2):

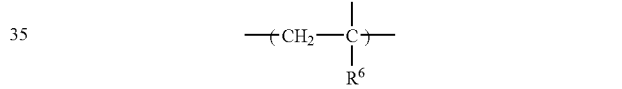

wherein $R^5$ represents a hydrogen atom or a methyl group and $R^6$ represents a phenyl group or a group represented by $-CO_2R^7$ wherein $R^7$ represents a substituted or unsubstituted alkyl group having from 1 to 12 carbon atoms, an alicyclic hydrocarbon or an aromatic hydrocarbon.

The nonspecific adsorption inhibitor of a substance relating to a living body concerned in this embodiment may contain the above-mentioned copolymer in a part thereof or may be constructed from the above-mentioned copolymer alone.

1.2. Physical Properties and Application of the Nonspecific Adsorption Inhibitor of a Substance Relating to a Living Body Regarding the nonspecific adsorption inhibitor of a substance relating to a living body concerned in the present embodiment, number average molecular weight of the above-mentioned copolymer is generally from 1,000 to 1,000,000, preferably from 2,000 to 100,000, more preferably from 3,000 to 50,000. Additionally, molecular weight distribution of the above-mentioned copolymer is typically from 1.5 to 3 as weight average molecular weight/number average molecular weight. This is because when number average molecular weight of the above-mentioned copolymer is less than the above-mentioned range, there is a case where the nonspecific adsorption inhibitory effect is insufficient. On the other hand, when number average molecular weight of the above-mentioned copolymer is larger than the above-mentioned range, there is a case where it becomes difficult to carry out the coating and handling because of the increased viscosity of the solution.

The copolymer, contained by the nonspecific adsorption inhibitor of a substance relating to a living body concerned in the present embodiment, is water-soluble. The "water-soluble" according to the present invention means that, when the copolymer is added to and mixed with water to a 1% polymer solid content at 25° C., it is dissolved therein transparently or semi-transparently as observed with the naked eye.

The nonspecific adsorption inhibitor of a substance relating to a living body concerned in the present embodiment has a high nonspecific adsorption inhibitory effect. The nonspecific adsorption inhibitor of a substance relating to a living body concerned in the present embodiment can illustratively act in the following manner.

According to the nonspecific adsorption inhibitor of a substance relating to a living body concerned in the present embodiment, the nonspecific adsorption inhibitor can be adhered to the wall surface of a container, a tool and the like through the hydrophobic bond of the repeating unit (B) of the above-mentioned copolymer, and nonspecific adsorption of protein, lipid and the like can also be inhibited because the wall surface becomes hydrophilic by the repeating unit (A).

Since the nonspecific adsorption inhibitor of a substance relating to a living body concerned in the present embodiment shows a high adsorption rate because of the possession of a copolymer in which the repeating unit (A) and repeating unit (B) are balanced, it particularly can effectively inhibit adsorption of protein and the like nonspecific adsorption-causing substances to the wall surface of a container, a tool and the like.

Additionally, according to the nonspecific adsorption inhibitor of a substance relating to a living body concerned in the present embodiment, the repeating unit (B) of the above-mentioned copolymer interacts with protein and the repeating unit (A) has the dispersing activity for water. Therefore, it can effect solubilization of protein in an aqueous solvent by preventing change of the protein to hydrophobic nature through its conformational change.

The nonspecific adsorption inhibitor of a substance relating to a living body concerned in the present embodiment shows the effect to strongly inhibit nonspecific adsorption of protein and the like, for example, by a method in which it is coated on a container, a tool and the like or a method in which it is added to a diluent, reaction solvent or preservative of a diagnostic agent. Namely, the method for coating an article according to an embodiment of the present invention comprises a step for allowing the article to contact with solution which comprises the nonspecific adsorption inhibitor of a substance relating a living body concerned in the present embodiment.

Also, the nonspecific adsorption inhibitor of a substance relating to a living body concerned in the present embodiment can inhibit signals of nonspecific analytes by its use as a diluent of an immuno-diagnostic agent.

Additionally, the nonspecific adsorption inhibitor of a substance relating to a living body concerned in the present embodiment has the effect to maintain activity of a protein for a prolonged period of time when it is added to solution of the protein as, for example, a stabilizer of a labeled antibody, a labeled antigen, an enzyme, a primary antibody or a primary antigen to be used as a clinical diagnostic agent, a stabilizer of a protein contained in a blood plasma preparations, a stabilizer of an enzyme or the like to be used in washing contact lenses, and the like.

1.3. Repeating Unit (A)

In the above-mentioned copolymer, the repeating unit (A) represented by the above-mentioned formula (1) can contribute to the expression of high nonspecific adsorption inhibitory effect.

Examples of the substituted or unsubstituted alkyl group having from 1 to 8 carbon atoms represented by $R^1$ and $R^2$ in the above-mentioned formula (1a) include a substituted or unsubstituted straight or branched alkyl group, such as a methyl group, an ethyl group, a n-propyl group, an isopropyl group, a n-butyl group, a sec-butyl group, a tert-butyl group, a pentyl group, a hexyl group, a heptyl group, an octyl group, and groups in which these groups are substituted with a functional group such as a hydroxyl group, an alkoxy group and the like.

More illustratively, it is preferable that, in the above-mentioned formula (1), $R^1$ represents a hydrogen atom or a methyl group and $R^2$ represents at least one species selected from a hydrogen atom, a methyl group and a hydroxyethyl group.

Additionally, examples of the ring structure which corresponds to the above-mentioned formula (1b) include a pyrrolidino group, a piperidino group, a morpholino group, a thiomorpholino group and the like.

1.4. Repeating Unit (B)

In the above-mentioned copolymer, the repeating unit (B) represented by the above-mentioned formula (2) can contribute to the expression of high nonspecific adsorption inhibitory effect by shifting the hydrophilic/hydrophobic balance of the copolymer to the hydrophobic side.

Examples of the substituted or unsubstituted alkyl group having from 1 to 12 carbon atoms represented by $R^5$ in the above-mentioned formula (2) include a substituted or unsubstituted straight or branched alkyl group such as a methyl group, an ethyl group, a n-propyl group, an isopropyl group, a n-butyl group, a sec-butyl group, a tert-butyl group, a pentyl group, a hexyl group, a heptyl group, an octyl group, and groups in which these groups are substituted with a functional group such as a hydroxyl group, an alkoxy group.

Also, examples of the alicyclic hydrocarbon represented by $R^7$ in the above-mentioned formula (2) include an isobonyl group and a cyclohexyl group, and examples of the aromatic hydrocarbon represented by $R^7$ include benzyl.

Also, it is preferable that, in the above-mentioned formula (2), $R^5$ represents a hydrogen atom or a methyl group, $R^6$ is a group represented by $-CO_2R^7$ and $R^7$ represents at least one species selected from a methyl group, an ethyl group and a methoxyethyl group.

Additionally, in the above-mentioned copolymer, at least one or more species of the repeating unit (A) and repeating unit (B) may be respectively contained. In this connection, the above-mentioned copolymer may contain a repeating unit (C) in addition to the repeating unit (A) and repeating unit (B).

1.5. Repeating Unit (C)

According to the nonspecific adsorption inhibitor of a substance relating to a living body concerned in the present embodiment, the above-mentioned copolymer can further contain a repeating unit (C) represented by the following formula (3):

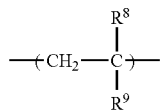

(3)

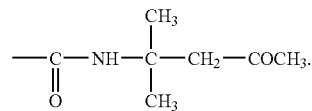

(8)

wherein $R^8$ represents a hydrogen atom or a methyl group and $R^9$ represents an organic group which comprises at least one aldo group or keto group. In the above-mentioned copolymer, the repeating unit (C) can contribute to increase in durability of a formed coating film (a nonspecific adsorption inhibitor layer).

According to the present invention, the aldo group means an aldehyde group bound to a carbon atom, the keto group means a carbonyl group bound to two carbon atoms, and carboxyl group and amino group are not included.

In the above-mentioned formula (3), $R^8$ is preferably a hydrogen atom. $R^9$ is preferably an organic group having an aldo group such as formyl group, formylphenyl group, an ester group containing an aldo group represented by the following formula (4):

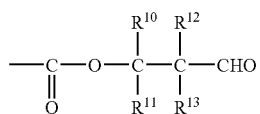

(4)

wherein $R^{10}$ to $R^{13}$ are independently a hydrogen atom, a methyl group or an ethyl group;
an amido group containing an aldo group represented by the following formula (5):

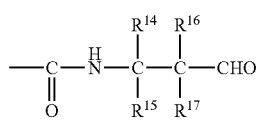

(5)

wherein $R^{14}$ to $R^{17}$ are independently hydrogen atom, methyl group or ethyl group, or the like;
or an organic group having a keto group such as an acetyl group, an acetylphenyl group, an ester group containing keto group represented by the following formula (6):

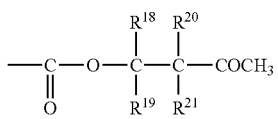

(6)

wherein $R^{18}$ to $R^{21}$ are independently a hydrogen atom, a methyl group or an ethyl group;
an amido group containing keto group represented by the following formula (7):

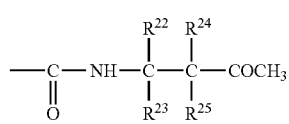

(7)

wherein $R^{22}$ to $R^{25}$ are independently a hydrogen atom, a methyl group or an ethyl group, or the like More preferable organic group as $R^9$ is a formyl group, an acetyl group and an organic group represented by the following formula (8) and most preferable organic group is the organic group represented by the following formula (8):

1.6. Hydrazide Compound (H)

The hydrazide compound (H) has at least two hydrazino groups per one molecule. Examples of a hydrazide compound (H) include dicarboxylic acid dihydrazide having from 2 to 10, particularly from 4 to 6 carbon atoms in total, such as oxalic acid dihydrazide, malonic acid dihydrazide, succinic acid dihydrazide, glutaric acid dihydrazide, adipic acid dihydrazide, sebacic acid dihydrazide, phthalic acid dihydrazide, isophthalic acid dihydrazide, terephthalic acid dihydrazide, maleic acid dihydrazide, fumaric acid dihydrazide, itaconic acid dihydrazide or the like; hydrazides having three or more of functional groups such as citric acid trihydrazide, nitriloacetic acid trihydrazide, cyclohexanetricarboxylic acid trihydrazide, ethylenediaminetetraacetic acid tetrahydrazide or the like; water-soluble dihydrazines such as aliphatic dihydrazines having from 2 to 4 carbon atoms and the like such as ethylene-1,2-dihydrazine, propylene-1,2-dihydrazine, propylene-1,3-dihydrazine, butylene-1,2-dihydrazine, butylene-1,3-dihydrazine, butylene-1,4-dihydrazine, butylene-2,3-dihydrazine and the like, and a compound in which at least a part of hydrazino groups of such a multifunctional hydrazine derivative is blocked by allowing them to react with carbonyl compound such as acetaldehyde, propionaldehyde, butylaldehyde, acetone, methyl ethyl ketone, diethyl ketone, methyl-n-propyl ketone, methyl-n-butyl ketone, diacetone alcohol or the like, such as adipic acid dihydrazide monoacetonehydrrazone, adipic acid dihydrazide diacetonehydrrazone and the like. Of these hydrazide compounds (H), at least one species selected from adipic acid dihydrazide, sebacic acid dihydrazide, isophthalic acid dihydrazide and adipic acid dihydrazide diacetonehydrrazone is preferable. The hydrazide compound (H) can be used alone or as a mixture of two or more species.

It is preferable that the amount of the hydrazide compound (H) to be used is such an amount that mol equivalent ratio of the total amount of an aldo group and a keto group in the above-mentioned copolymer to the hydrazino group of the hydrazide compound (H) becomes a range of 1:0.1 to 5, preferably becomes a range of 1:0.5 to 1.5, further preferably becomes a range of 1:0.7 to 1.2. In this case, when the hydrazino group is less than 1 equivalent based on 1 equivalent as the total of an aldo group and a keto group, the formed coat (nonspecific adsorption inhibitor layer) becomes inferior in durability in some cases. On the other hand, when it exceeds 5 equivalents, the nonspecific adsorption inhibitory effect lowers in some cases.

Although the hydrazide compound (H) can be blended at an optional step for preparing the nonspecific adsorption inhibitor of a substance relating to a living body concerned in the present embodiment, in order to keep polymerization stability at the time of producing the above-mentioned copolymer, it is preferable to blend total amount of the hydrazide compound (H) after production of the above-mentioned copolymer.

The hydrazide compound (H) has the activity to form a hydrophilic network structure to effect crosslinking of the nonspecific adsorption inhibitor layer, through the reaction of its hydrazino group with the keto group and/or aldo group of the above-mentioned copolymer at the drying step after application of the nonspecific adsorption inhibitor of a substance relating to a living body concerned in the present embodiment. Although the crosslinking reaction generally proceeds at ordinary temperature without using a catalyst, it can be accelerated by adding catalyst such as a water-soluble metal salt or the like such as zinc sulfate, manganese sulfate, cobalt sulfate or the like, or by carrying out drying by heating.

2. Production of Nonspecific Adsorption Inhibitor of a Substance Relating to a Living Body Next, the monomer composition to be used for producing the above-mentioned copolymer is described.

2.1. Monomer (a)

The repeating unit (A) has a structure derived from at least one species of a monomer (a). It is preferable that the monomer (a) is at least one species of monomer selected from acrylamide and N-substituted monomers of acrylamide.

Examples of the N-substituted monomers of acrylamide include N,N-dimethylacrylamide, N,N-diethylacrylamide, N-isopropylacrylamide, N-hydroxyethylacrylamide, acryloylmorpholine, acryloylpyrrolidine, acryloylpiperidine and the like.

More preferable examples of the monomer (a) include at least one species selected from acrylamide, N-hydroxyethylacrylamide and N,N-dimethylacrylamide, and further preferable examples include N,N-dimethylacrylamide or a combination of N,N-dimethylacrylamide and N,N-diethylacrylamide.

2.2. Monomer (b)

The repeating unit (B) has a structure derived from at least one species of a monomer (b). The monomer (b) is at least one species of monomer of which solubility in water is less than 20%.

According to the present invention, the "monomer of which solubility in water is less than 20%" means a monomer in which separation of the monomer from water phase can be confirmed with the naked eye after adding it to water of 25° C. to be a monomer concentration of 20% followed by stirring.

Since solubility of the monomer (b) in water is less than 20%, further high nonspecific adsorption inhibitory effect can be expressed.

Examples of the monomer (b) include methoxyethyl (meth)acrylate, methyl (meth)acrylate, ethyl (meth)acrylate, propyl (meth)acrylate, butyl (meth)acrylate, 2-ethylhexyl (meth)acrylate, lauryl(meth)acrylate, cyclohexyl(meth)acrylate, isobonyl(meth)acrylate, benzyl(meth)acrylate, styrene and the like. More preferable monomer (b) is at least one species selected from methyl methacrylate, ethyl acrylate and methoxyethyl acrylate.

2.3. Monomer Composition and Polymerization

According to the nonspecific adsorption inhibitor of a substance relating to a living body concerned in the present embodiment, it may contain a repeating unit (C) and may further contain a repeating unit (D), in addition to the repeating unit (A) and repeating unit (B).

A monomer (c) is a component for forming the repeating unit (C), and a monomer (d) is a component for forming the repeating unit (D). Namely, the repeating unit (C) has a structure derived from at least one species of the monomer (c). The repeating unit (D) has a structure derived from at least one species of the monomer (d).

It is preferable that the monomer (c) is at least one species selected from acrolein, formylstyrene, vinyl methyl ketone, vinyl phenyl ketone, (meth)acrylate and (meth)acrylamides having a group represented by the above-mentioned formulae (4) to (7). It is more preferable that the monomer (c) is at least one species selected from acrolein, vinyl methyl ketone and diacetone acrylamide in view of copolymerizability. It is most preferable that the monomer (c) is diacetone acrylamide in view of the safety of monomer.

When from 1 to 10% by weight of an anionic monomer, particularly styrenesulfonic acid, isoprenesulfonic acid, 2-acrylamido-2-methylpropanesulfonic acid or the like, is used as the other monomer (d) and copolymerized with the monomer (a) and monomer (b) (further with the monomer (c) as occasion demands) to produce a copolymer, and the product is used as the diluent of an immuno-diagnostic agent, the effect to inhibit signals of nonspecific analytes can be obtained in some cases.

The monomer composition for producing the above-mentioned copolymer is preferably from 30 to 99% by weight of the monomer (a), from 1 to 70% by weight of the monomer (b), from 0 to 49% by weight of the monomer (c) and from 0 to 49% by weight of the other monomer (d), more preferably from 40 to 95% by weight of the monomer (a), from 5 to 60% by weight of the monomer (b), from 0 to 30% by weight of the monomer (c) and from 0 to 20% by weight of the other monomer (d), based on 100% by weight of the total monomers. The monomer composition in the case of particularly requiring durability is preferably from 30 to 97% by weight of the monomer (a), from 1 to 68% by weight of the monomer (b), from 2 to 49% by weight of the monomer (c) and from 0 to 49% by weight of the other monomer (d), based on 100% by weight of the total monomers.

When the monomers (a) and (b) are outside the above-mentioned ranges, the nonspecific adsorption inhibitory becomes inferior in some cases. Also, when the monomer (c) is less than 2% by weight, the durability becomes inferior in some cases, and when it exceeds 49% by weight, the nonspecific adsorption inhibitory becomes inferior in some cases.

The monomers to be used can be used in the copolymerization by purifying those which are available as industrial materials or without purification as such.

Polymerization of the monomers can be carried out by, for example, conventionally known polymerization methods such as radical polymerization, anionic polymerization, cationic polymerization and the like, of which radical polymerization is preferable in view of the easy production.

Additionally, polymerization of the monomers is carried out by stirring and heating them together with conventionally known solvent, initiator, chain transfer agent and the like. The polymerization time is generally from 30 minutes to 24 hours and the polymerization temperature is approximately from 0 to 120° C.

It is preferable that the copolymer aqueous solution after polymerization is purified by dialysis membrane, Dialyzer, Acilyzer and the like.

3. Examples and Comparative Examples

Although the following describes the present invention further in detail with reference to examples, the present invention is not limited by these.

In the Examples, weight average molecular weight (Mw) and number average molecular weight (Mn) were measured by a gel permeation chromatography (GPC) which uses a monodisperse system polyethylene glycol as the standard, using TSK gel α-M column manufactured by Tosoh Corporation, under analytical conditions of 1 mL/min in flow rate, 0.1 mM sodium chloride aqueous solution/acrylonitrile mixed solvent as the elution solvent and 40° C. as the column temperature. The absorbance was measured by Model 680 Micro Plate Reader manufactured by Nippon Bio-Rad Laboratories.

3.1. Example 1

3.1.1 Synthesis of Nonspecific Adsorption Inhibitor (N-1)

With 900 g of water, 60 g of dimethylacrylamide and 30 g of diethylacrylamide as the monomer (a), 10 g of methyl methacrylate as the monomer (b) and 1 g of cysteamine hydrochloride as a chain transfer agent were mixed and put into a separable flask equipped with a stirrer. With bubbling nitrogen into this, temperature of the contents was risen to be 70° C., 2 g of 2,2'-azobis(2-methylpropionamidine)dihydrochloride was added as an initiator, followed by polymerization for 2 hours. The temperature was further increased to be 80° C. to carry out 3 hours of aging and then lowered to room temperature. The obtained copolymer solution was purified by a Dialyzer and further freeze-dried to obtain 95 g of the nonspecific adsorption inhibitor (N-1) of the Example.

Number average molecular weight of the nonspecific adsorption inhibitor (N-1) by GPC was 8,000, and its weight average molecular weight was 16,000.

3.1.2. Measurement of Nonspecific Adsorption Inhibitory Effect

A 96 well plate made of polystyrene (to be referred to as "96 well plate" hereinafter) was filled with a 0.5% aqueous solution of the nonspecific adsorption inhibitor (N-1) and incubated at 37° C. for 30 minutes followed by washing 5 times with ion exchange water. Next, the 96 well plate was filled with a horseradish peroxidase-labeled mouse IgG antibody ("AP124P" manufactured by Millipore) aqueous solution and incubated at room temperature for 30 minutes followed by washing three times with PBS buffer. Then a color was developed with TMB (3,3',5,5'-tetramethylbenzidine)/hydrogen peroxide aqueous solution/sulfuric acid to measure the absorbance at 450 nm.

3.2. Examples 2 and 3

The same operation as Example 1 was carried out except that monomers were used at the monomer ratios shown in Table 1.

3.3. Comparative Example 1

A copolymerization polymer (X-1) was obtained by the same method as "3.1.1 Synthesis of nonspecific adsorption inhibitor (N-1)" in Example 1, except that 100 g of diethylacrylamide alone was used as the monomer instead of 60 g of dimethylacrylamide and 30 g of diethylacrylamide as the monomer (a) and 10 g of methyl methacrylate as the monomer (b).

Number average molecular weight of the copolymerization polymer (X-1) by GPC was 5,200, and its weight average molecular weight was 13,000.

Also, the absorbance when the copolymerization polymer (X-1) was used was measured by the same method as the "3.1.2. Measurement of nonspecific adsorption inhibitory effect".

3.4. Comparative Example 2

A copolymerization polymer (X-2) was obtained by the same method as "3.1.1 Synthesis of nonspecific adsorption inhibitor (N-1)" in Example 1, except that 100 g of dimethylacrylamide alone was used as the monomer instead of 60 g of dimethylacrylamide and 30 g of diethylacrylamide as the monomer (a) and 10 g of methyl methacrylate as the monomer (b).

Number average molecular weight of the copolymerization polymer (X-2) by GPC was 9,800, and its weight average molecular weight was 20,000.

Also, the absorbance when the copolymerization polymer (X-2) was used was measured by the same method as the "3.1.2. Measurement of nonspecific adsorption inhibitory effect".

3.5. Comparative Example 3

In Example 1, bovine serum albumin (BSA) was used instead of the nonspecific adsorption inhibitor (N-1), and the absorbance when BSA was used was measured by the same method as the "3.1.2. Measurement of nonspecific adsorption inhibitory effect".

3.6. Comparative Example 4

In Example 1, the same method as "3.1.1 Synthesis of nonspecific adsorption inhibitor (N-1)" was carried out except that 100 g of methyl methacrylate alone was used as the monomer instead of 60 g of dimethylacrylamide and 30 g of diethylacrylamide as the monomer (a) and 10 g of methyl methacrylate as the monomer (b). However, since a large amount of white coagulation were generated several minutes after addition of the initiator, the polymerization was stopped.

3.7. Comparative Example 5

In Example 1, commercially available polyvinyl pyrrolidone was used instead of the nonspecific adsorption inhibitor (N-1). The absorbance when BSA was used was measured by the same method as the "3.1.2. Measurement of nonspecific adsorption inhibitory effect".

3.8. Measured Results

Measured results on the nonspecific adsorption inhibitory effect of the above Examples and Comparative Examples are shown in Table 1.

TABLE 1

|  | Monomer (a) | Monomer (b) | Molecular Weight (Mn) | Absorbance |
|---|---|---|---|---|
| Example 1 | Dimethylacrylamide Diethylacrylamide | Methyl methacrylate | 8000 | 0.026 |
| Example 2 | Acryloylmorpholine 95 g | Methyl methacrylate 5 g | 6100 | 0.060 |
| Example 3 | Dimethylacrylamide 90 g | Methyl methacrylate 10 g | 5000 | 0.081 |

TABLE 1-continued

| | Monomer (a) | Monomer (b) | Molecular Weight (Mn) | Absorbance |
|---|---|---|---|---|
| Comparative Example 1 | Diethylacrylamide | none | 5200 | 0.21 |
| Comparative Example 2 | Dimethylacrylamide | none | 9800 | 1.8 |
| Comparative Example 3 | Bovine serum albumin (nonspecific adsorption inhibitor) | | — | 0.20 |
| Comparative Example 4* | none | Methyl methacrylate 100 g | — | — |
| Comparative Example 5 | Commercial polyvinyl pyrrolidone (a water-soluble polymer having a ring structure other than that of the present invention in a side chain) | | 40000 | 2.4 |

According to Table 1, it was confirmed that the amount of nonspecific adsorption of mouse IgG antibody to the 96 well plate can be markedly reduced by the use of the nonspecific adsorption inhibitor of a substance relating to a living body concerned in Examples 1 to 3, in comparison with the case of a high polymer derived from diethylacrylamide or dimethylacrylamide alone which corresponds to the monomer (a) or bovine serum albumin.

3.9. Example 4

3.9.1. Synthesis of Nonspecific Adsorption Inhibitor (N-4)

A nonspecific adsorption inhibitor (N-4) as a copolymerization polymer was obtained by the same method as "3.1.1 Synthesis of nonspecific adsorption inhibitor (N-1)" in Example 1, except that 56 g of dimethylacrylamide and 16 g of diethylacrylamide were used as the monomer (a), and 8 g of methyl methacrylate as the monomer (b) and 20 g of diacetone acrylamide as the monomer (c), instead of the use of 60 g of dimethylacrylamide and 30 g of diethylacrylamide as the monomer (a) and 10 g of methyl methacrylate as the monomer (b).

Number average molecular weight of the nonspecific adsorption inhibitor (N-4) by GPC was 9,000, and its weight average molecular weight was 25,000.

Also, the absorbance when the nonspecific adsorption inhibitor (N-4) was used was measured by the same method as the "3.1.2. Measurement of nonspecific adsorption inhibitory effect".

3.9.2. Measurement of Nonspecific Adsorption Inhibitory Effect After Washing With Surfactant A 96 well plate was filled with a 0.5% aqueous solution of the nonspecific adsorption inhibitor (N-4) and incubated at 37° C. for 30 minutes, followed by washing with ion exchange water. The remaining water was blown off with an air gun. It was dried at 40° C. for 3 hours. It was further washed three times with polyoxyethylene sorbitan monolaurate which is a surfactant. Next, the 96 well plate was filled with a horseradish peroxidase-labeled mouse IgG antibody ("AP124P" manufactured by Millipore) aqueous solution and incubated at room temperature for 30 minutes, followed by washing three times with PBS buffer. Then a color was developed with TMB (3,3',5,5'-tetramethylbenzidine)/hydrogen peroxide aqueous solution/sulfuric acid to measure the absorbance at 450 nm.

3.10. Example 5

By adding 1 g of adipic acid dihydrazide to 10 g of the nonspecific adsorption inhibitor (N-4) and by using a 0.55% aqueous solution containing the nonspecific adsorption inhibitor (N-4) and adipic acid dihydrazide, measurement of the nonspecific adsorption inhibitory effect and measurement of the nonspecific adsorption inhibitory effect after washing with the surfactant were carried out.

3.11. Comparative Example 6

Using BSA, measurement of the nonspecific adsorption inhibitory effect and measurement of the nonspecific adsorption inhibitory effect after washing with the surfactant were carried out.

3.12. Measured Results

Measured results of the above Examples 4 and 5 and Comparative Example 6 are shown in Table 2.

TABLE 2

| | Nonspecific adsorption inhibitory effect | |
|---|---|---|
| | No surfactant | After washing with surfactant |
| Example 4 | 0.024 | 1.7 |
| Example 5 | 0.028 | 0.087 |
| Comparative Example 6 | 0.20 | 2.4 |

According to Table 2, it was confirmed that the amount of nonspecific adsorption after washing with the surfactant can be markedly reduced by the use of the nonspecific adsorption inhibitor of a substance relating to a living body concerned in Examples 4 and 5, in comparison with the case of the use of BSA in Comparative Example 6. Particularly, according to Example 5, it was confirmed that the nonspecific adsorption after washing with the surfactant can be markedly reduced by the use of the nonspecific adsorption inhibitor containing a hydrazide compound (H).

According to the above-mentioned nonspecific adsorption inhibitor of a substance relating to a living body, it has a high nonspecific adsorption inhibitory effect because it comprises a copolymer comprising a repeating unit (A) represented by the above-mentioned formula (1) and a repeating unit (B) represented by the above-mentioned formula (2).

Although the present invention has been described in detail with reference to specific examples in the foregoing, it is apparent to person skilled in the art that it is possible to add various alterations and modifications insofar as the alterations and the modifications do not deviate from the spirit and scope of the present invention.

This patent application is based on Japanese Patent Application No. 2007-291793 filed on Nov. 9, 2007 and Japanese Patent Application No. 2008-61119 filed on Mar. 11, 2008 and the contents thereof are incorporated herein by reference.

What is claimed is:

1. A method of inhibiting the adsorption of lipids and/or proteins to an article, comprising:
   (1) allowing the article to contact an aqueous solution comprising a water-soluble copolymer, wherein the water-soluble copolymer comprises:
      (i) a repeating unit (A) derived from at least one species of monomer (a) and represented by formula (1):

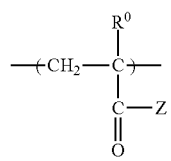

(1)

wherein $R^0$ represents a hydrogen atom or a methyl group and Z represents a group represented by formula (1a) or (1b):

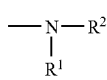

(1a)

wherein $R^1$ and $R^2$ independently represent a hydrogen atom, an alkyl group having from 1 to 8 carbon atoms or an alkyl group having from 1 to 8 carbon atoms which is substituted with at least one group selected from a hydroxyl group, a carboxyl group, an alkoxy group, an acyloxy group and an alkoxycarbonyl group;

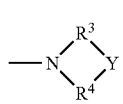

(1b)

wherein $R^3$ and $R^4$ independently represent single bond, methylene, methylene substituted with a hydroxyl group or a carboxyl group, an alkylene group having from 2 to 7 carbon atoms or an alkylene group having from 2 to 7 carbon atoms substituted with a hydroxyl group or carboxyl group wherein total number of carbon atoms of $R^3$ and $R^4$ is from 4 to 10; wherein at least one of $R^3$ and $R^4$ may have an ether bond, and Y represents any one of a single bond, O and S; and (ii) a repeating unit (B) derived from at least one species of a monomer (b) and represented by formula (2):

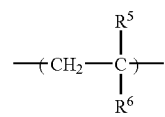

(2)

wherein $R^5$ represents a hydrogen atom or a methyl group; and $R^6$ represents phenyl group or a group represented by —$CO_2R^7$ wherein $R^7$ represents an unsubstituted alkyl group having from 1 to 12 carbon atoms, an alicyclic hydrocarbon, an aromatic hydrocarbon, or an alkyl group having from 1 to 12 carbon atoms substituted with a hydroxyl group or carboxyl group, wherein the amount of monomer (a) in the water-soluble copolymer is 30 to 99% by weight and the amount of monomer (b) in the water-soluble copolymer is 1 to 70% by weight; and (iii) a repeating unit (C) represented by the following formula (3):

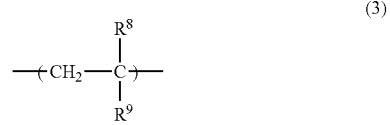

(3)

wherein
$R^8$ represents a hydrogen atom or a methyl group and
$R^9$ represents an organic group which comprises at least one aldo group or keto group a formyl group, a formylphenyl group, a group presented by formula (4), a group represented by formula (5), an acetyl group, an acetylphenyl group, a group represented by formula (6) or a group represented by formula (7):

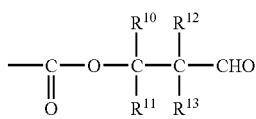

(4)

wherein $R^{10}$ to $R^{13}$ are independently a hydrogen atom, a methyl group or an ethyl group;

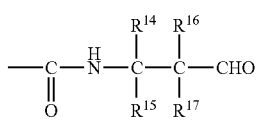

(5)

wherein $R^{14}$ to $R^{17}$ are independently a hydrogen atom, methyl group or ethyl group;

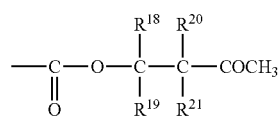

(6)

wherein $R^{18}$ to $R^{21}$ are independently a hydrogen atom, a methyl group or an ethyl group;

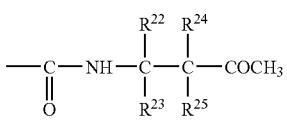

(7)

wherein $R^{22}$ to $R^{25}$ are independently a hydrogen atom, a methyl group or an ethyl group; followed by (2) contacting the article with at least one lipid, protein or a mixture thereof, wherein the copolymer inhibits non-specific adsorption of lipids and proteins to the article.

2. The method of claim 1, wherein $R^1$ represents a hydrogen atom or a methyl group and $R^2$ represents at least one species selected from a hydrogen atom, a methyl group and a hydroxyethyl group.

3. The method of claim 2, wherein repeating unit (B) is derived from at least one monomer having a solubility in water of less than 20%.

4. The method of claim 1, wherein repeating unit (B) is derived from at least one monomer having a solubility in water of less than 20%.

5. The method of claim 1, wherein
$R^5$ represents a hydrogen atom or a methyl group;
$R^6$ represents —$CO_2R^7$; and
$R^7$ represents at least one species selected from a methyl group, ethyl group and methoxyethyl group.

6. The method of claim 1, wherein the water-soluble copolymer is reacted with at least one a hydrazide compound (H) that comprises at least two hydrazino groups per one molecule; and wherein the water-soluble copolymer is crosslinked by the reaction of a hydrazino group with a keto and/or aldo group of the water-soluble copolymer.

7. The method of claim 6, wherein the hydrazide compound comprises at least one member selected from the group consisting of (1) dicarboxylic hydrazides having from 2 to 10 carbon atoms in total, (2) hydrazides having three or more functional groups, (3) water-soluble dihydrazides and (4) a compound in which at least a part of the hydrazine groups of a multifunctional hydrazine derivative is blocked by allowing them to react with a carbonyl compound.

8. The method of claim 1, wherein the adsorption of lipids to the article is inhibited.

9. The method of claim 1, wherein the adsorption of proteins to the article is inhibited.

10. The method of claim 1, wherein the adsorption of an antibody to the article is inhibited.

11. The method of claim 1, wherein the water-soluble copolymer is adhered to the article through the hydrophobic bond of the repeating unit (B).

12. The method of claim 1, wherein the amount of monomer (a) in the water-soluble copolymer is 40 to 95% by weight and the amount of monomer (b) in the water-soluble copolymer is 5 to 60% by weight.

13. The method of claim 1, which comprises contacting the article with at least one lipid.

14. The method of claim 1, which comprises contacting the article with at least one protein.

15. The method of claim 14, wherein the protein is an antibody.

16. The method of claim 1, wherein the article is a biochip.

17. The method of claim 1, wherein the article is composed of polystyrene.

18. The method of claim 1, wherein the article is a polystyrene plate containing wells.

19. The method of claim 1, further comprising, between (1) and (2), washing the article with water.

* * * * *